United States Patent [19]

McPherson

[11] Patent Number: 5,133,712
[45] Date of Patent: Jul. 28, 1992

[54] HAIR GRASPING DEVICE
[75] Inventor: Bruce McPherson, Maitland, Fla.
[73] Assignee: Selvac Corporation, Dresher, Pa.
[21] Appl. No.: 578,693
[22] Filed: Sep. 6, 1990
[51] Int. Cl.⁵ .............................................. A61B 17/41
[52] U.S. Cl. ...................................... 606/43; 606/133; 606/210
[58] Field of Search .................. 606/36, 43, 133, 206, 606/210; 219/230; 81/484, 487, 491

[56] References Cited

U.S. PATENT DOCUMENTS

| | | | |
|---|---|---|---|
| 1,974,106 | 9/1934 | Gardella | 606/210 |
| 2,113,962 | 4/1938 | Moir | 606/133 X |
| 2,888,927 | 6/1959 | Fozard | 606/43 |
| 4,078,569 | 3/1978 | Hoshi | 606/43 |
| 4,524,648 | 6/1985 | Chung | 606/210 X |

FOREIGN PATENT DOCUMENTS

| | | | |
|---|---|---|---|
| 431364 | 9/1948 | Italy | 606/43 |
| 172275 | 8/1960 | Switzerland | 606/133 |

*Primary Examiner*—Lee S. Cohen
*Attorney, Agent, or Firm*—Panitch Schwarze Jacobs & Nadel

[57] ABSTRACT

A hair grasping device includes a pair of hair engaging surfaces spring biased to a closed or engaged position in which a hair is grasped therebetween. The device further includes a first clamping member which is pivotally disposed with respect to a housing. The first clamping member includes the first hair engaging surface. A spring disposed within the housing biases the first hair engaging surface toward the second hair engaging surface of a second clamping member. A thumb wheel is employed to pivot the first clamping member against the bias of the spring. The thumb wheel is also used to actuate a switch which connects a high frequency energy source to one of the hair engaging surfaces to destroy the papilla area of a grasped hair.

16 Claims, 1 Drawing Sheet

HAIR GRASPING DEVICE

FIELD OF THE INVENTION

The present invention relates to a hair grasping device and, more particularly, to a hair grasping device for holding a hair while high frequency electrical energy is applied thereto.

BACKGROUND OF THE INVENTION

Many different types of devices have been used in an effort to permanently remove unwanted hair. Most of the more recently developed devices used high frequency electricity in an effort to destroy the papilla area at the base of the hair shaft. While these devices have proved effective, they have not all been user friendly.

For instance, in one technique a needle is inserted into the follicle adjacent the hair in an effort to reach the papilla area. High frequency electrical energy is then applied through the needle in an effort to destroy the hair producing papilla area. The more generally used type of such devices has a needle which is used in combination with a tweezer. The drawback of these devices is that the insertion of the needle under the skin may produce irritation and swelling, and burning of the tissues.

More recently, hair removal devices use an electrically charged tweezer, which grips the hair at a short distance from the skin. High frequency electrical energy is then directly applied to the hair, wherein the high frequency energy travels down the hair shaft to the papilla area. Since there is no requirement for insertion of a needle into the skin, soreness and irritation of tissue are eliminated. However, this type of device requires more time for hair removal, and, consequently, the user is required to physically compress the tweezers during this time. As such, the user having to firmly grip the tweezers, will eventually become tired, thereby, inhibiting substantial continuous use of the device. In addition, due to the shape of the tweezer grasping end, it is difficult to see the hair the user is trying to grasp. A hair removal device of this type is disclosed in U.S. Pat. No. 4,174,713, which is hereby incorporated by reference.

A first embodiment hair removing device of my invention is disclosed in U.S. patent application Ser. No. 319,610, filed Mar. 6, 1989, U.S. Pat. No. 4,884,061 which is incorporated by reference. The present application discloses a new embodiment device of my invention.

My inventions overcome many of the disadvantages inherent in the above-described hair removal devices of others by providing hair grasping devices which are conducive to continuous use without tiring the operator. My hair grasping devices are spring biased to a closed position or a position in which a hair is grasped. Consequently, while high frequency electrical energy is applied to the hair, the user does not have to actuate the grasping device. Moreover, my devices are particularly applicable to the elderly or arthritic user who may not be able to put forth the energy necessary to squeeze a pair of tweezers for a considerable length of time.

The hair grasping devices embodying my inventions are adapted to be hand held. More particularly, the hand held devices are adapted to be used in either the right or left hand. Moreover, the user can readily view and access the hair to be grasped, thereby preventing the user from becoming frustrated.

My new design is an improvement over my original design in that it is easier to use generally and equally easy to use with either hand.

SUMMARY OF THE INVENTION

Briefly stated, my present invention is a hair grasping device for hair removal. The device comprises a housing, a first clamping member having a first hair engaging surface and a second clamping member supported by at least a portion of the housing and including a second hair engaging surface. The first clamping member is pivotally disposed with respect to the housing. The device also comprises a biasing means and an actuating means. The biasing means biases the first clamping member and first hair engaging surface toward the second hair engaging surface for grasping and holding a hair therebetween. The actuating means is movably disposed with respect to the housing for pivoting the first clamping member against the bias of the biasing means and the first hair engaging surface away from the second hair engaging surface.

In another aspect, my present invention is a hair grasping device for grasping and holding a hair while high frequency electrical energy is applied thereto. The device comprises a housing including an aperture and an opening. The device further comprises a first clamping member including a first hair engaging surface outside the housing. The first clamping member is pivotally disposed with respect to the housing and at least a portion of the first clamping member extends through the opening. The device further comprises a second clamping member supported by at least a portion of the housing and including a second hair engaging surface. At least one of the hair engaging surfaces is comprised of an electrically conductive material. The device further comprises biasing means, thumb wheel means and switch means. The biasing means is for biasing the first clamping member towards the second clamping member for grasping and holding a hair between the first and second hair engaging surfaces. The thumb wheel means is pivotally disposed with respect to the housing for pivoting the first clamping member against the bias of the biasing means and the first hair engaging surface away from the second hair engaging surface. At least a portion of the thumb wheel means protrudes from the housing through the aperture. The switch means is positioned to be actuated by the thumb wheel means for supplying an electrical energy signal to the electrically conductive material.

In another aspect, my present invention is a hair grasping device for hair removal. The device comprises a housing and first and second clamping members. The first clamping member is movably disposed with respect to the housing and includes a first hair engaging surface. The second clamping member is supported by at least a portion of the housing and includes a second hair engaging surface. The device further comprises biasing means and actuating means. The biasing means biases the first clamping member towards the second clamping member and the first hair engaging surface towards the second hair engaging surface for grasping and holding a hair therebetween. The actuating means is pivotally disposed with respect to the housing for moving the first clamping member against the bias of the biasing means and the first hair engaging surface away from the second hair engaging surface.

BRIEF DESCRIPTION OF THE DRAWINGS

The foregoing summary, as well as the following detailed description of a preferred embodiment, will be better understood when read in conjunction with the appended drawings. For the purpose of illustrating the invention, there is shown in the drawings an embodiment which is presently preferred, it being understood, however, that the invention is not limited to the specific methods and instrumentalities disclosed. In the drawings.

DESCRIPTION OF PREFERRED EMBODIMENT

Figure 1:
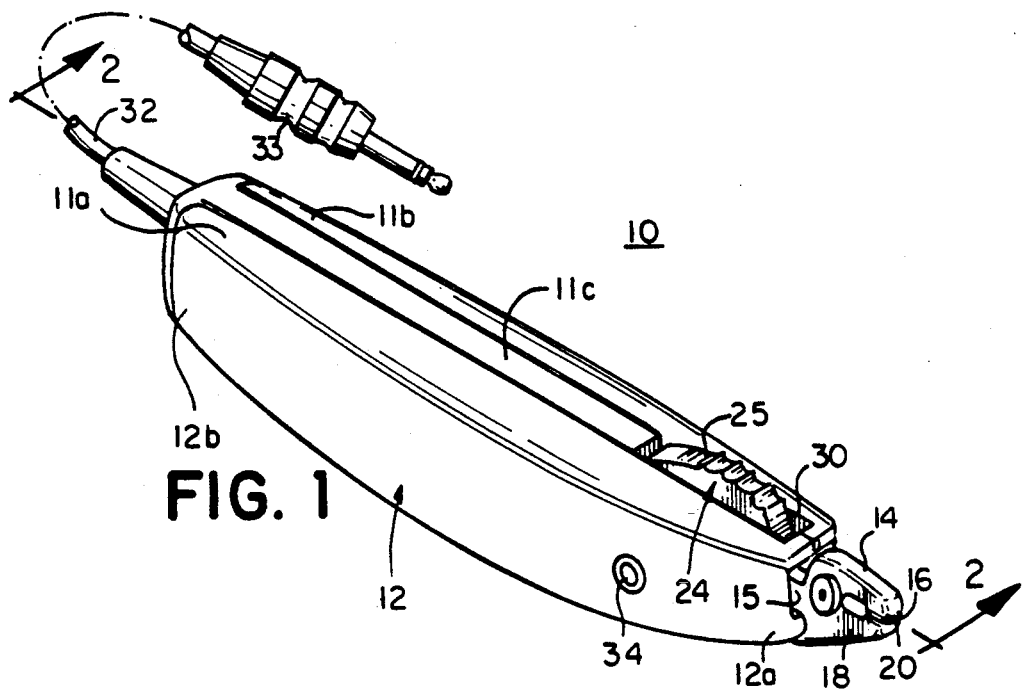
FIG. 1 is a perspective view of a hair grasping device in accordance with the present invention.

Certain terminology is used in the following description for convenience only and should not be considered limiting. For example, the words "right," "left," "lower" and "upper" designate directions in the drawings to which reference is made. The words "inwardly" and "outwardly" refer to directions toward and away from, respectively, the geometric center of the hair grasping device and designated parts thereof. Said terminology includes the words above specifically mentioned, derivatives thereof and words of similar import.

Referring to the drawings in detail, wherein like numerals indicate like elements throughout, there is shown in FIGS. 1 through 4 a presently preferred embodiment of a hair grasping device in accordance with the invention.

Referring to FIG. 1, a hair grasping device generally designated 10 is shown. Hair grasping device 10 includes an elongated housing 12 curved or otherwise shaped generally so as to fit comfortably within the hand of a user. Housing 12 includes a first end 12a and a second end 12b. The first end 12a has an opening 15. The precise shape of housing 12 has advantages in that it is equally conducive to both right-hand and left-hand use. However, it is within the spirit and scope of the invention to construct housing 12 of any conventional shape conducive to being comfortably hand held, such as the shape of a pocket knife or other such hand held tool or device. In the present embodiment, housing 12 is preferably in the form of two similarly shaped half sections 11a, 11b and a central hollow frame 11c, which are constructed of injection-molded, high strength plastic material. Half sections 11a and 11b are normally secured by ultrasonic welding with the frame 11c. However, it is also within the spirit and scope of the invention to form housing 12 and/or secure housing sections 11a, 11b and 11c together in some other manner.

Figure 2:
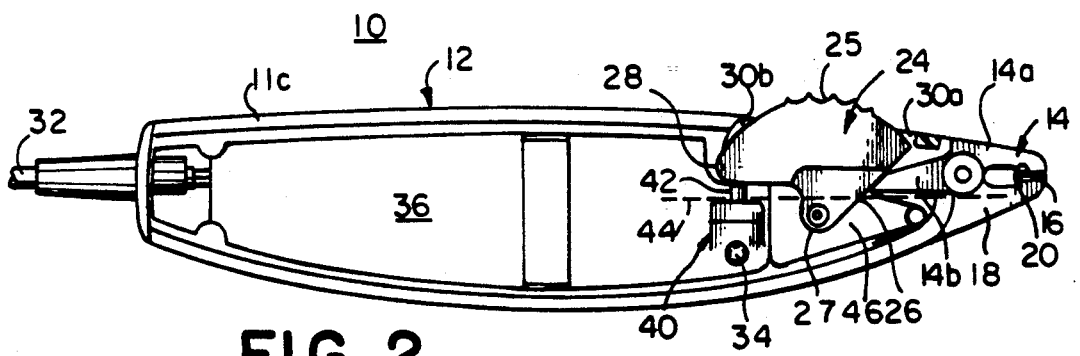
FIG. 2 is a sectional view of the device of FIG. 1 taken along line 2—2 showing the clamping member of the device in a closed position.
Figure 3:
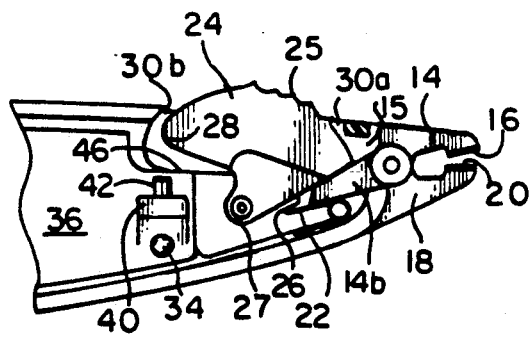
FIG. 3 is a fragmented view of an end of the device of FIGS. 1 and 2 showing clamping members of the device in an open position.
Figure 4:
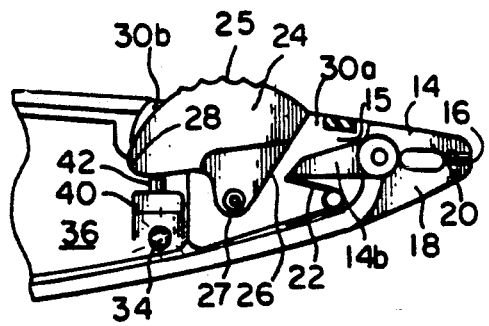
FIG. 4 is a fragmented view of an end of the device of FIGS. 1 and 2 showing the switch which controls the high frequency energy source actuated.

The interior of housing 12 is shown in FIGS. 2, 3 and 4. Housing 12 includes an opening 15. A first clamping member 14 is movably disposed with respect to the housing 12, preferably at least partially disposed in the housing 12 extending through opening 15, such that first clamping member 14 is partially supported, preferably pivotally supported within housing 12. Adjacent first clamping member 14 is a second clamping member 18.

First clamping member 14 is preferably U- or yoke-shaped with a single portion 14a projecting from the housing 12 and a pair of arms 14b extending around a pivot and a portion of the housing frame 11c projecting from the first end of 12a of the housing 12. Second clamping member 18, in the present embodiment, is preferably formed by the projection of the frame 11c of the housing and is supported by the contiguous portion of the frame 11c clamped between sections 11a and 11b at the forward end 12a of the housing. However, it is understood by those skilled in the art, that second clamping member 18 could be disposed in any fashion that complements the movement of first clamping member 14—pivotally or otherwise and may be a separate component.

First and second clamping members 14 and 18 include opposed first and second hair engaging surfaces 16 and 20, respectively, for clamping, engaging or grasping a hair to be removed. Preferably, the hair engaging surface 20 of clamping member 18 comprises an electrically conductive material for receiving and applying high frequency electrical energy to a hair disposed between the clamping members 14 and 18. The electrically conductive material of hair engaging surface 20 is preferably a beryllium copper alloy or some other material conducive to transmitting high frequency electrical energy. Preferably, the second hair engaging surface is provided in part by an exposed end of a generally L-shaped metal rod 44 indicated in phantom in FIG. 2, which extends from the second hair engaging surface 20 through frame 11c to a printed circuit board ("PCB") subassembly indicated generally at 36. The first hair engaging surface 16 of first clamping member 14 may be made of any electrically nonconductive material such as a high strength plastic material from which that member may also be made.

Biasing means is employed for biasing the first clamping member 14 toward the second clamping member 18 and the first hair engaging surface 16 toward and, preferably, into engagement with the second hair engaging surface 20 for grasping and holding a hair (not shown) therebetween. Preferably, the biasing means comprises a pair of identical springs 22, one of which can be seen in the figures. A second, identical spring 22 is positioned identically on an opposite (hidden) side of the housing frame 11c. Each spring 22 is preferably positioned between portion of the housing 12 and the first clamping member 14 and/or actuating means, preferably a thumb wheel 24. The spring 22 is under a predetermined initial compression when the hair engaging surfaces 16 and 20 are in engagement (see FIG. 2) to provide the hair engaging surfaces 16 and 20 with sufficient compressive force to firmly grasp and hold therebetween the hair to be removed. The magnitude of the grasping or compressive force may be sufficient to allow the user to remove a hair by "plucking", without applying electrical energy. On the other hand, the compressive force is not so great as to damage the hair to the point where its electrical conductivity is inhibited.

Movably disposed with respect to housing 12 is an actuating means actuating the device 10. Preferably, the actuating means is a thumb wheel 24 supported pivotally within the housing 12. Housing 12 includes a generally elongate, slot-like aperture 30, preferably located along the top center of the housing 12, through which at least a portion of the thumb wheel 24 protrudes.

As shown in FIGS. 2, 3, and 4, thumb wheel 24 preferably includes four sides or faces 25, 26, 27 and 28 serving four distinct purposes. Now referring to FIGS. 2, 3 and 4, side 25 of thumb wheel 24 projects through the aperture 30 and contains parallel ridges for engagement with the user's thumb (not shown). The ridges are generally designed and provided to prevent the user's thumb from slipping off thumb wheel 24 while operating the hair grasping device 10. Preferably, thumb wheel 24 is U- or yoke-shaped with side 25 connecting two identical arms each including sides 26-28. The arms straddle a portion of the housing frame 11c extending from the area of the PCB assembly 36 to the second clamping member 18. Preferably, a generally U- or yoke-shaped brass shield 46 is also mounted over that portion of the housing frame 11c extending between the PCB assembly 36 and the second clamping member 18, beneath the arms of the thumb wheel 24. Side 26 of thumb wheel 24 is flat yet angled to complement an extreme end of leg 14b of first clamping member 14. Side 26 is flat so to securely engage leg 14b of first clamping member 14 when resting in a neutral position (see FIG. 2) or when in a forwardmost position after moving first clamping member 14 against the bias of the spring 22 (see FIG. 3). Side 27 is rounded to economize on space and provide a means for the thumb wheel 24 to be pivotally and securely mounted within the housing 12. Similarly, side 28 is contoured to contact and cam a biased switch actuating member 42 (see FIG. 4) of a switch 40 in a rear position of the thumb wheel to activate the switch 40. For purposes of the remaining discussion, when necessary, thumb wheel 24 will be specifically referred to by its component sides.

Elongate aperture 30 has a first end 30a and a second end 30b. The first end 30a of aperture 30 is positioned closer to the first end 12a of housing 12 than is the second end 30b of aperture 30. Second end 30b of aperture 30 is positioned closer to the second end 12b of housing 12 than is the first end 30a of aperture 30.

When thumb wheel 24 is in the neutral or middle position, the hair engaging surfaces 16 and 20 are in a "closed" position, preferably in engagement with each other as shown in FIG. 2. When thumb wheel 24 is rotated forward toward the first end 30a of aperture 30, side 26 cams leg 14a of first clamping member 14, moving, in particular, pivoting first clamping member 14 against the bias of spring 22 and, consequently, the first hair engaging surface 16 away from the second surface 20. The surfaces 16 and 20 disengage and separate and are in a fully open position as shown in FIG. 3, at the extreme forward travel of thumb wheel 24. When the thumb wheel 24 is rotated rearward, toward the second end 30b of aperture 30, biased actuating member 42 is contacted or engaged and, subsequently, depressed (see FIG. 4) such that switch 40 and associated PCB assembly 36 on which switch 40 is mounted is actuated for supplying an electrical energy signal, preferably a high frequency electrical energy signal, from a source (not depicted) to the rod 44 providing the electrically conductive material of the second hair engaging surface 20. When thumb wheel 24 is released from a forward or backward position, either the spring 22 or the biased actuating member 42, respectively, will bias thumb wheel 24 back into its neutral position. Thus, the position of thumb wheel 24 controls and corresponds not only to the relative position of first clamping member 14 to second clamping member 18 and the positions of hair engaging surfaces 16 and 20, but also to the actuation of the switch 40.

Referring now to FIG. 2, hair grasping device 10 is preferably connected to an electrical energy source (not shown), preferably of high frequency electrical energy, through a coaxial cable 32 having a connector end 33. Cable 32 includes a casing, which is constructed of insulative material such as PVC, or any other nonconductive material. The interconnections between the coaxial cable 32 and the circuitry on the PCB assembly 36 are conventional and can be obtained, for example, by referring to the same structures and connections as described in the parent patent application Ser. No. 319,610, which is incorporated by reference herein.

Referring now to FIGS. 2 and 4, actuating member 42 is biased up towards the aperture 30 such that it is not depressed and thus unactuated when the thumb wheel 24 is either in the forward position with clamping members 14 and 18 and hair engaging surfaces 16 and 20 disengaged or in the middle, neutral position with clamping members 14 and 18 and hair engaging surfaces 16 and 20 engaged. However, when thumb wheel 24 is moved to the reverse position, side 28 of thumb wheel 24 engages biased actuating member 42 and subsequently depresses the actuating member 42 which, in turn, actuates the switch 40. When actuated, switch 40 preferably begins a cycle wherein high frequency electrical energy emanates from hair engaging surface 20 for a period of time which can be adjusted at the electrical source. The remaining portions of the PCB assembly 36 are of conventional structure and, accordingly, their details do not form any part of the instant invention. The switch 40 may be, for example, a single pole, single throw, key switch, like an Omron Electronics, Inc. Model B3F-3150, which is internally biased open and momentarily closed by depression of its actuating member 42.

In use, the user or operator rotates thumb wheel 24 forward, toward the first end 30a of aperture 30, to open or separate hair engaging surfaces 16 and 20 (see FIG. 3). The operator then presses the hair grasping device 10 down against the skin with hair engaging surfaces 16 and 20 positioned about the hair to be removed. Thumb wheel 24 is then released and the biasing action of spring 22 brings hair engaging surfaces 16 and 20 into engagement (see FIG. 2) with the hair, thereby grasping and holding the hair therebetween. The user then rotates the thumb wheel 24 rearward towards the second end 30b of aperture 30 until side 28 of thumb wheel 24 engages and depresses actuation member 42 to the point where switch 40 is activated. Preferably, light 34, an LED, which is part of the assembly 36 and is viewable through a side wall 11a (or 11b) of the housing 12, illuminates upon the activation of switch 40 and remains illuminated until a cycle time has expired. Upon the thumb wheel 24 actuating switch 40, assembly 36 begins the hair removal process by applying high frequency electrical energy to the hair which is transmitted to the papilla area of the hair in the manner described in detail in the above referenced U.S. Pat. No. 4,174,713. When light 34 is no longer illuminated the user knows the cycle time has expired and the hair can be pulled out. To remove the hair from between hair engaging surfaces 16 and 20, the operator again rotates thumb wheel 24 forward toward the first end 30a of aperture 30 and against the biasing action of spring 22 to separate hair engaging surfaces 16 and 20.

From the foregoing description it can be seen that the present invention comprises a hair grasping device which is biased into a hair grasping or closed position, thereby being conducive to continuous use without tiring the operator. It will be recognized by those skilled in the art that changes may be made to the above-described embodiment of the invention without departing from the broad inventive concepts thereof. For example, the hair grasping device 10 may be used for removal of hair without the application of high frequency energy (i.e., plucking). It is understood, therefore, that this invention is not limited to the particular embodiments disclosed, but is intended to cover all modifications which are within the spirit and scope of the invention as defined by the appended claims.

I claim:

1. A hair grasping device for hair removal comprising:
   a housing;
   a first clamping member pivotally disposed with respect to said housing and including a first hair engaging surface;
   a second clamping member supported by at least a portion of the housing and including a second hair engaging surface, at least one of said hair engaging surfaces comprising an electrically conductive material;
   biasing means for biasing said first clamping member and said first hair engaging surface toward said second hair engaging surface for grasping and holding a hair therebetween;
   actuating means movably disposed with respect to said housing for pivoting said first clamping member against the bias of said biasing means and the first hair engaging surface away from the second hair engaging surface; and
   switch means for supplying an electrical signal to said electrically conductive material, said switch means being controlled by the position of said actuating means.

2. The hair grasping device as recited in claim 1 wherein said second hair engaging surface is fixedly positioned with respect to said housing.

3. The hair grasping device as recited in claim 1 wherein said biasing means comprises a spring disposed between said housing and at least one of said actuating means and said first clamping member.

4. The hair grasping device as recited in claim 1 wherein said actuating means has three positions, a first position wherein said actuating means moves the first clamping member against the bias of said biasing means, a second position wherein said actuating means actuates said switch means, and a neutral position between the first and second positions.

5. The hair grasping device as recited in claim 4 wherein said actuating means is a thumb wheel supported pivotally within said housing.

6. The hair grasping device as recited in claim 1 wherein said actuating means is a thumb wheel supported pivotally within said housing.

7. A hair grasping device for grasping and holding a hair while high frequency electrical energy is applied thereto, said device comprising:
   a housing including an aperture and an opening;
   a first clamping member pivotally disposed with respect to said housing, at least a portion of said first clamping member extending through said opening and including a first hair engaging surface outside of said housing;
   a second clamping member supported by at least a portion of the housing and including a second hair engaging surface, at least one of said hair engaging surfaces being comprised of an electrically conductive material;
   biasing means for biasing said first clamping member toward said second clamping member for grasping and holding a hair between said first and second hair engaging surfaces;
   thumb wheel means pivotally disposed with respect to said housing for pivoting said first clamping member against the bias of said biasing means and said first hair engaging surface away from said second hair engaging surface, at least a portion of said thumb wheel means protruding from said housing through said aperture; and
   switch means positioned to be actuated by said thumb wheel means for supplying an electrical energy signal to the electrically conductive material.

8. The hair grasping device as recited in claim 7 wherein said second hair engaging surface is positioned fixedly with respect to said housing.

9. The hair grasping device as recited in claim 7 wherein said biasing means comprises a spring disposed between said housing and at least one of said first clamping member and said thumb wheel means.

10. The hair grasping device as recited in claim 7 wherein said thumb wheel means has at least three positions, a first position wherein said thumb wheel means moves the first clamping member against the bias of said biasing means, a second position wherein said thumb wheel means actuates said switch means, and a third, neutral position between the first and second positions.

11. A hair grasping device for hair removal comprising:
   a housing;
   a first clamping member movably disposed with respect to said housing and including a first hair engaging surface;
   a second clamping member supported by at least a portion of the housing and including a second hair engaging surface, at least one of said hair engaging surfaces comprising an electrically conductive material;
   biasing means for biasing said first clamping member toward said second clamping member and said first hair engaging surface toward said second hair engaging surface for grasping and holding a hair therebetween;
   actuating means pivotally disposed with respect to said housing for moving said first clamping member against the bias of said biasing means and the first hair engaging surface away from the second hair engaging surface; and
   switch means for supplying an electrical energy signal to said electrically conductive material, said switch means being controlled by the position of said actuating means.

12. The hair grasping device as recited in claim 11 wherein said second clamping member is fixedly positioned with respect to said housing.

13. The hair grasping device as recited in claim 11 wherein said biasing means comprises a spring disposed between said housing and at least one of said actuating means and said first clamping member.

14. The hair grasping device as recited in claim 11 wherein said actuating means has three positions, a first position wherein said actuating means moves the first clamping member against the bias of said biasing means, a second position wherein said actuating means actuates said switch means, and a third neutral position between the first and second positions.

15. The hair grasping device as recited in claim 14 wherein said actuating means is a thumb wheel supported pivotally within said housing.

16. The hair grasping device as recited in claim 11 wherein said actuating means is a thumb wheel supported pivotally within said housing.

* * * * *